United States Patent
Wahl et al.

(10) Patent No.: US 10,307,191 B2
(45) Date of Patent: Jun. 4, 2019

(54) SUBTALAR PLATE IMPLANT

(71) Applicant: NuVISTA LLC, Carlsbad, CA (US)

(72) Inventors: Rebecca H. Wahl, Escondido, CA (US); Bruce R. Lawrence, Oceanside, CA (US)

(73) Assignee: In2Bones USA, LLC, Memphis, TN (US)

( * ) Notice: Subject to any disclaimer, the term of this patent is extended or adjusted under 35 U.S.C. 154(b) by 702 days.

(21) Appl. No.: 14/830,525

(22) Filed: Aug. 19, 2015

(65) Prior Publication Data

US 2017/0049492 A1 Feb. 23, 2017

(51) Int. Cl.
*A61B 17/80* (2006.01)

(52) U.S. Cl.
CPC .............................. *A61B 17/8061* (2013.01)

(58) Field of Classification Search
CPC . A61B 17/80; A61B 17/8052; A61B 17/8057; A61B 17/8061
USPC ...................... 606/70, 71, 280–299, 902–906
See application file for complete search history.

(56) References Cited

U.S. PATENT DOCUMENTS 8,784,498 B2 * 7/2014 Scheland ........... A61B 17/8061
606/280

* cited by examiner

Primary Examiner — Eric S Gibson
(74) Attorney, Agent, or Firm — Rutan & Tucker, LLP

(57) ABSTRACT

A subtalar plate implant (12) for correcting and/or altering the alignment of a hyperpronated foot (10) comprises a plate portion (22) and an insert portion (24) that is connected to the plate portion (22). The plate portion (22) is selectively attachable to a lateral aspect of the calcaneus (16). The insert portion (24) is positionable within the subtalar joint (18). The insert portion (24) includes a top surface (236) that is selectively positionable substantially adjacent to a base of the talus (14), the top surface (236) being angled to allow the talus (14) to articulate over the top surface (236). The insert portion (24) further includes a bottom surface (238) that is selectively positionable substantially adjacent to a dorsal surface of the calcaneus (16). The insert portion (24) can include a groove (356) that is formed along the bottom surface (238) substantially parallel to the plate portion (22).

17 Claims, 8 Drawing Sheets

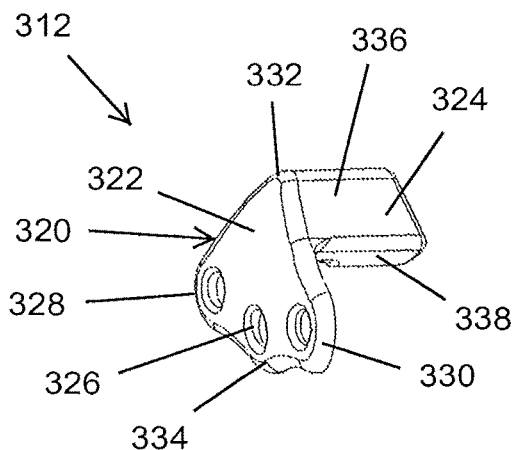
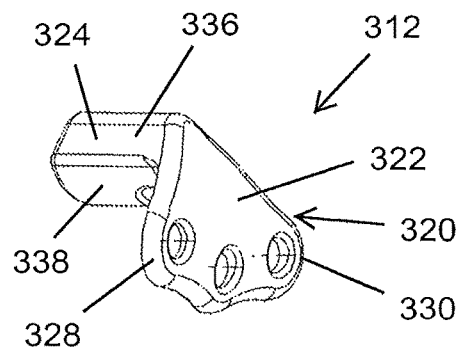
Fig. 3A        Fig. 3B
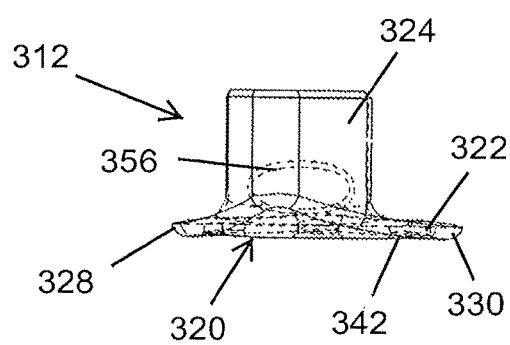
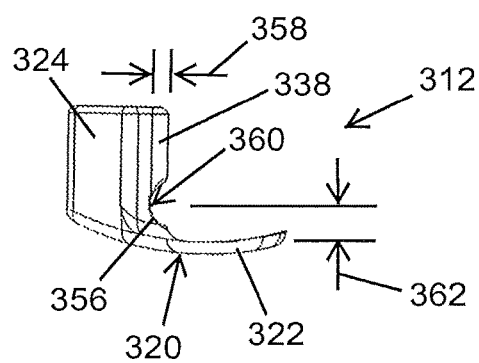
Fig. 3C        Fig. 3D
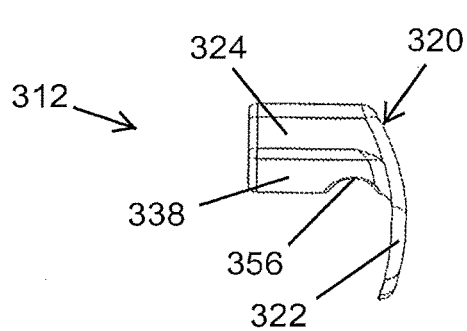
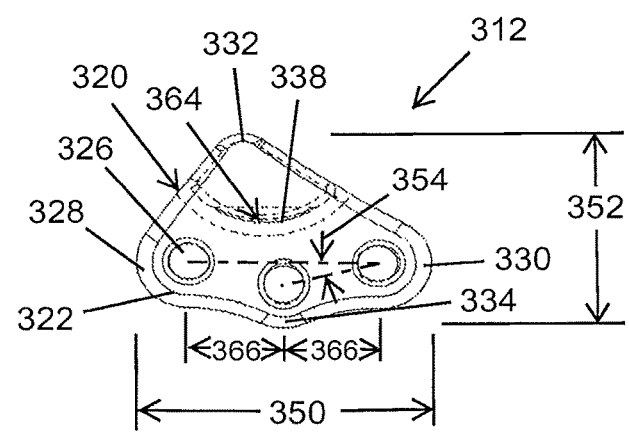
Fig. 3E        Fig. 3F Fig. 5A                    Fig. 5B

SUBTALAR PLATE IMPLANT

RELATED APPLICATION

The application claims priority on U.S. Provisional Application Ser. No. 61/765,603 filed on Feb. 15, 2013, entitled "SUBTALAR PLATE IMPLANT". As far as is permitted, the contents of U.S. Provisional Application Ser. No. 61/765,603 are incorporated herein by reference.

BACKGROUND

In human anatomy, the subtalar joint is a joint of the foot that occurs at the meeting point of the talus and the calcaneus. The main ligament of the subtalar joint, i.e. the interosseous talocalcaneal ligament, runs through the sinus tarsi, which is a canal between the articulations of the talus and the calcaneus. The subtalar joint has several important functions, including adapting to changes in terrain while walking, pivoting one's body while on their feet, and shock absorption as one's feet hit the ground. As such, the subtalar joint can be said to perform two basic types of motion within the foot, pronation, which is the natural motion that occurs when one's instep rolls inward, and supination, which relates to motion in the opposite direction as the foot rolls outward and the arch height increases. Unfortunately, certain problems can occur within the subtalar joint, including excessive pronation or hyperpronation, which occurs when the inward motion of the ankle bone is excessive and goes past the healthy point necessary for its intended functions. This excessive motion is caused by a misalignment between the ankle bones and the hindfoot bones, e.g., the talus and the calcaneus. It creates an imbalance of forces and weight distribution in the foot that propagates throughout the entire body. Over time, this functional imbalance causes repetitive damage to joints, ligaments, tendons, and bone structures. Left untreated, hyperpronation can lead to foot ailments such as bunions, heel pain (plantar fasciitis), hammertoes, and various other foot ailments. Furthermore, the excessive motion in the foot can travel up the body and cause knee, hip and lower back pain. Accordingly, a means to effectively treat and/or correct for hyperpronation is desired to inhibit any such problems.

SUMMARY

The present invention is directed toward a subtalar plate implant for implanting in a foot, the foot including a talus, a calcaneus, and a subtalar joint at the meeting point of the talus and the calcaneus. In certain embodiments, the subtalar plate implant comprises a plate portion and an insert portion that is connected to the plate portion. The plate portion is selectively positionable substantially adjacent to a lateral aspect of the calcaneus. Additionally, the plate portion includes an aperture that is adapted to receive an attacher for selectively attaching the plate portion to the lateral aspect of the calcaneus. The insert portion is at least partially positionable within the subtalar joint when the subtalar plate implant is implanted in the foot.

As provided in detail herein, the subtalar plate implant is an extraarticular subtalar joint axis-altering arthroereisis implant. The implant can be used in the sinus tarsi of the foot, i.e. in the canal between the articulations of the talus and the calcaneus, to correct and/or alter the alignment of a hyperpronated foot. The subtalar joint is a complex joint that is positioned below the ankle joint. The subtalar joint is comprised of the calcaneus and the talus. It is also known as the talocalcaneal joint and is comprised of three separate articulations between the two bones referred to as the posterior, middle, and anterior facets.

Arthroereisis procedures, including the use arthroereisis implants, can be used to restrict the excess pronation of the subtalar joint in an attempt to hold it in a corrected position, while still preserving supination of the subtalar joint. Stated in another manner, the use of a subtalar arthroereisis implant helps to block or restrict motion between the talus and the calcaneus and beyond, while preserving the subtalar joint itself. Thus, not only does the arthroereisis implant restrict excessive pronation, but it allows adequate motion for normal foot function, thus permitting growth and adaption of the hindfoot and midfoot joints in more functionally correct realignment without invading any of the joints.

In one embodiment, the plate portion is shaped to substantially match a shape of the lateral aspect of the calcaneus adjacent to which the plate portion is selectively positionable. Additionally, the plate portion can be substantially amorphous-shaped. For example, in one embodiment, the plate portion includes a first end, a second end, a top and a bottom. Further, in such embodiment, the plate portion can include an aperture that is positioned substantially adjacent to each of the first end and the second end, and an aperture that is positioned substantially adjacent to one of the top and the bottom.

Additionally, in one embodiment, the insert portion includes a top surface that is selectively positionable substantially adjacent to a base of the talus, the top surface being angled to allow the talus to articulate over the top surface.

Further, in certain embodiments, the insert portion includes a bottom surface that is selectively positionable substantially adjacent to a dorsal surface of the calcaneus. Moreover, the insert portion can include a groove that is formed along the bottom surface. The groove can be formed along the bottom surface substantially parallel to the plate portion. In alternative embodiments, the bottom surface can be substantially convex-shaped, or the bottom surface can include a pair of flat segments that are angled relative to one another.

In another application, the present invention is directed toward a subtalar plate implant for correcting the hyperpronation of a foot, the foot including a talus, a calcaneus, and a subtalar joint at the meeting point of the talus and the calcaneus, the subtalar plate implant comprising an insert portion that is at least partially positionable within the subtalar joint when the subtalar plate implant is implanted in the foot, the insert portion including a bottom surface that is selectively positionable substantially adjacent to a dorsal surface of the calcaneus, and the insert portion including a groove that is formed along the bottom surface.

In still another application, the present invention is further directed toward, a subtalar plate implant for correcting the hyperpronation of a foot, the foot including a talus, a calcaneus, and a subtalar joint at the meeting point of the talus and the calcaneus, the subtalar plate implant comprising (i) a plate portion that is selectively positionable substantially adjacent to a lateral aspect of the calcaneus, the plate portion being substantially amorphous-shaped, the plate portion including a first end, a second end, a top and a bottom, wherein the plate portion includes an aperture that is positioned substantially adjacent to each of the first end and the second end, and wherein the plate portion includes an aperture that is positioned substantially adjacent to one of the top and the bottom, each of the apertures being adapted to receive an attacher for selectively attaching the plate portion to the lateral aspect of the calcaneus; and (ii) an insert portion that is connected to the plate portion, the insert portion extending substantially perpendicularly away from the plate portion, the insert portion including a top surface and a bottom surface, wherein the top surface is selectively positionable substantially adjacent to a base of the talus, the top surface being angled to allow the talus to articulate over the top surface; and wherein the bottom surface is selectively positionable substantially adjacent to a dorsal surface of the calcaneus, the insert portion including a groove that is formed along the bottom surface substantially parallel to the plate portion.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3A is a simplified perspective view of another embodiment of the subtalar plate implant;

FIG. 3B is another simplified perspective view of the subtalar plate implant of FIG. 3A;

FIG. 3C is a simplified end view of the subtalar plate implant of FIG. 3A;

FIG. 3D is a simplified side view of the subtalar plate implant of FIG. 3A;

FIG. 3E is another simplified side view of the subtalar plate implant of FIG. 3A;

FIG. 3F is a simplified top view of the subtalar plate implant of FIG. 3A;

FIG. 5A is a simplified side view of yet another embodiment of the subtalar plate implant;

FIG. 5B is another simplified side view of the subtalar plate implant of FIG. 5A;

DESCRIPTION

Figure 1A:
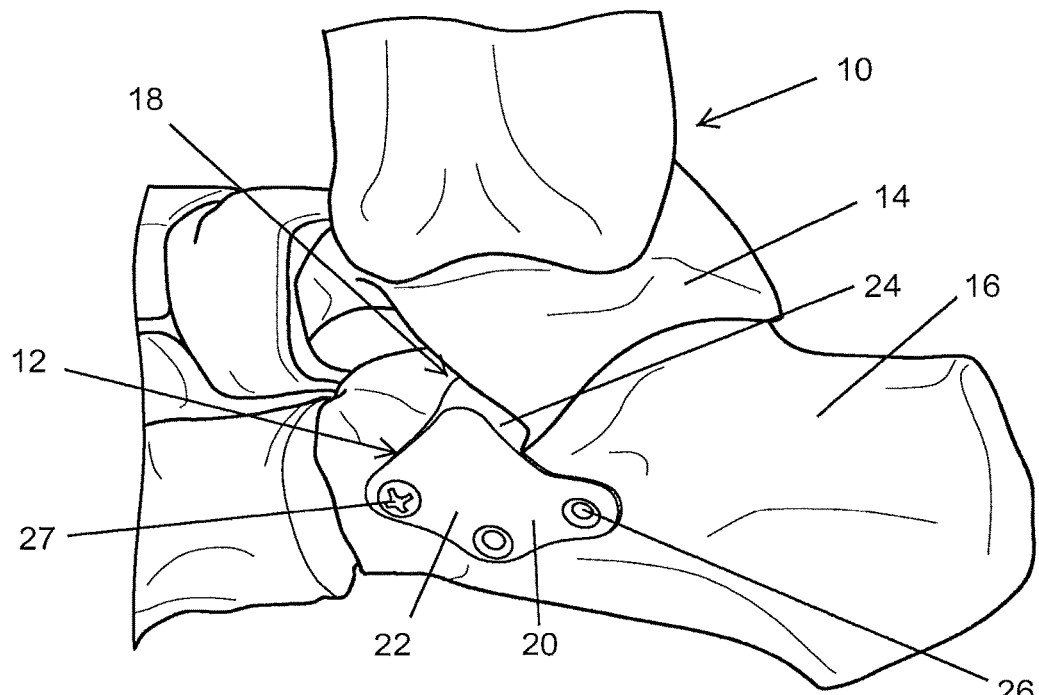
FIG. 1A is a perspective view of a portion of a foot and an embodiment of a subtalar plate implant having features of the present invention implanted therein.

FIG. 1A is a perspective view of a portion of a foot 10 and an embodiment of a subtalar plate implant 12 having features of the present invention implanted therein. More particularly, FIG. 1A illustrates the talus 14 and the calcaneus 16 of the foot 10, and the subtalar plate implant 12 that is implanted within the subtalar joint 18 at the meeting point of the talus 14 and the calcaneus 16.

It should be appreciated that certain soft tissue structures and the fibula have been omitted from FIG. 1A for purposes of clarity, i.e. so that the subtalar plate implant 12 can be better seen implanted within the subtalar joint 18.

The design and size of the subtalar plate implant 12 can be varied to suit the specific size and design requirements of the subtalar joint 18 into which the subtalar plate implant 12 will be implanted and/or to accommodate different foot anatomies. In the embodiment illustrated in FIG. 1A, the subtalar plate implant 12 comprises an implant body 20 including a plate portion 22 and an insert portion 24 that extends away from the plate portion 22.

As an overview, the subtalar plate implant 12 is uniquely designed to effectively treat and/or correct for hyperpronation of the foot 10. More particularly, as described in detail herein, the subtalar plate implant 12 is a subtalar axis-altering arthroereisis implant that can be used in the sinus tarsi of the foot 10, i.e. in the canal between the articulations of the talus 14 and the calcaneus 16, to correct and/or alter the alignment of a hyperpronated foot, while still preserving other normal functions of the subtalar joint 18, e.g., supination. For example, in various embodiments, when the subtalar plate implant 12 is implanted within the foot 10, the insert portion 24 of the implant body 20 is positioned substantially within the sinus tarsi and/or the subtalar joint 18 between the talus 14 and the calcaneus 16.

It should be appreciated that the implanting of the subtalar plate implant 12 within the subtalar joint 18 accomplishes the desired correcting and/or altering of the alignment of the foot 10 without requiring any associated fusion of the subtalar joint 18. Thus, the subtalar plate implant 12 provided herein properly changes the path of the movement of the talus 14 relative to the calcaneus 16. Further, the subtalar plate implant 12 is uniquely designed to provide stable correction to the subtalar joint 18 and proper alignment of the talus 14 and the calcaneus 16, while preserving joint motion.

Additionally, the implant body 20 can incorporate various design features, e.g., surface textures, sizes, shapes, and/or other desired design features, which can be varied to accommodate the individual patient into whom the subtalar plate implant 12 is being implanted. For example, in some embodiments, the implant body 20 can have a substantially smooth surface so as to inhibit any discomfort felt by the patient into whom the subtalar plate implant 12 is implanted. Further, the shape of the implant body 20, i.e. the shape of the plate portion 22 and/or the insert portion 24, can be varied to match the anatomical features of the talus 14 and the calcaneus 16 in the specific areas into which and/or adjacent to which the subtalar plate implant 12 is implanted. Moreover, edges and/or corners of the implant body 20 can be somewhat curved or rounded to further suit the comfort of the patient into whom the subtalar plate implant 12 is being implanted.

Still further, the implant body 20 can be formed from one or more suitable materials. For example, in certain embodiments, the plate portion 22 and/or the insert portion 24 of the implant body 20 can be made from one or more metal or polymeric materials. More specifically, in some non-exclusive alternative embodiments, the metal materials that may be used for the plate portion 22 and/or the insert portion 24 of the implant body 20 can include medical grade stainless steel, titanium alloy, and/or cobalt chrome alloy. Additionally, in other non-exclusive alternative embodiments, the polymeric materials that may be used for the plate portion 22 and/or the insert portion 24 of the implant body 20 can include polyethylene or polyether ether ketone (PEEK) implant grade materials. Still additionally and/or alternatively, the plate portion 22 and/or the insert portion 24 of the implant body 20 can be formed from other suitable materials.

In certain embodiments, the plate portion 22 of the implant body 20 may be shaped to at least substantially match the anatomy, i.e. the shape, of the lateral aspect of the calcaneus 16 in the area where the subtalar plate implant 12 is implanted. Stated in another manner, the plate portion 22 can be shaped to match the anatomy and/or shape of the lateral aspect of the calcaneus 16 adjacent to which the plate portion 22 is positioned when the subtalar plate implant 12 is implanted within the foot 10. Moreover, in alternative embodiments, the plate portion 22 can be formed to have any desired thickness so as to effectively maintain the structural integrity of the plate portion 22 and/or the subtalar plate implant 12, while still allowing for the desired comfort for the patient into whom the subtalar plate implant 12 is implanted.

Additionally, as shown in FIG. 1A, the plate portion 22 of the implant body 20 can include one or more apertures 26. Each of the apertures 26 is designed and/or adapted to receive an attacher 27, e.g., a screw, that will be inserted into the calcaneus 16 to secure the subtalar plate implant 12 in place, i.e. with the plate portion 22 positioned substantially adjacent to an area of the lateral aspect of the calcaneus 16. In the embodiment illustrated in FIG. 1A, the plate portion 22 includes three apertures 26 for receiving up to three attachers 27 (only one is illustrated in FIG. 1A). Alternatively, the plate portion 22 can include greater than three or less than three apertures 26, and/or the subtalar plate implant 12 can be secured in place with greater than three or less than three attachers 27.

With this design, the plate portion 22 can be fixedly secured to a lateral aspect of the calcaneus 16 outside of, but adjacent to the subtalar joint 18. As a result thereof, the subtalar plate implant 12 is can be relatively easily secured to the calcaneus 16 with the insert portion 24 accurately positioned in the subtalar joint 18. With this design, the plate portion 22 is outside the subtalar joint 18 while the insert portion 24 is positioned directly in the subtalar joint 18.

Stated in another fashion, the insert portion 24 is placed into the sinus tarsi and the plate portion 22 is fixed to the adjacent lateral calcaneus. With this design, the subtalar plate implant 12 is placed in the sinus tarsi effectively elevating the floor of the sinus tarsi which then changes the axis of the subtalar joint 18.

As noted above, and as illustrated in FIG. 1A, the insert portion 24 extends away from the plate portion 22. Still further, the insert portion 24 is sized and shaped to fit securely within the sinus tarsi and/or within the subtalar joint 18 when the subtalar plate implant 12 is implanted within the foot 10. As provided herein, when the subtalar plate implant 12 is implanted within the foot 10 of a person, the insert portion 24 is sized and shaped so that the insert portion 24 can be positioned within the sinus tarsi and/or the subtalar joint 18 in a manner so as to correct and/or alter the alignment of the foot 10, e.g., to correct and/or alter the alignment of a hyperpronated foot.

Additionally, as provided herein, in certain embodiments, a top surface 236 (illustrated in FIG. 2A) of the insert portion 24 can be positioned substantially adjacent to a base of the talus 14, and may be angled to allow the talus 14 to articulate over the top surface 236 in a corrected position to correct hyperpronation of the foot 10. Stated in another manner, the top surface 236 of the insert portion 24 can be positioned and shaped so as to allow the talus 14 to rotate over the top surface 236 and relative to the calcaneus 16 during movement of the subtalar joint 18, e.g., during walking or other flexing of the foot 10. Further, in some embodiments, a bottom surface 238 (illustrated in FIG. 2A) of the insert portion 24 may be shaped to at least substantially match the anatomy of the calcaneus 16 in the area of the calcaneus 16 adjacent to which the insert portion 24 is positioned.

In certain embodiments, the insert portion 24 can be fixedly secured to the plate portion 22. Alternatively, in some embodiments, the insert portion 24 can be integrally formed with the plate portion 22.

Figure 1B:
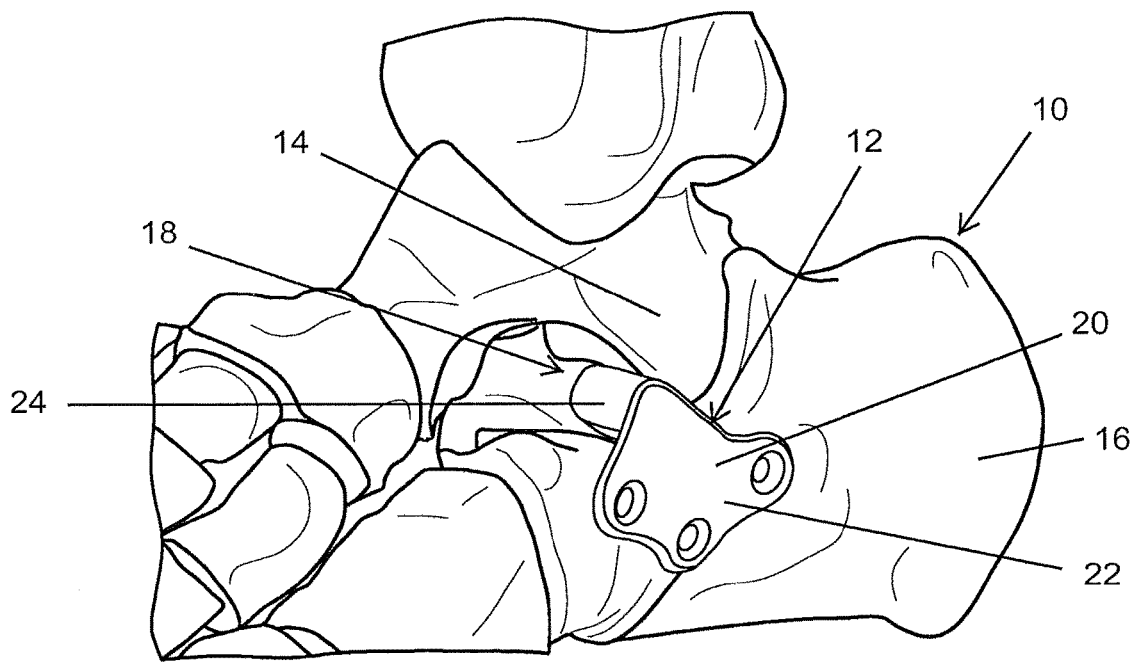
FIG. 1B is another perspective view of a portion of the foot and the subtalar plate implant of FIG. 1A implanted therein.

FIG. 1B is another perspective view of a portion of the foot 10 and the subtalar plate implant 12 of FIG. 1A implanted therein. In particular, FIG. 1B illustrates more clearly how the insert portion 24 of the implant body 20 is positioned securely within the sinus tarsi and/or within the subtalar joint 18 when the subtalar plate implant 12 is implanted within the foot 10. Moreover, FIG. 1B also more clearly illustrates (i) how the plate portion 22 can be sized and shaped to match the anatomy and/or shape of the lateral aspect of the calcaneus 16 adjacent to which the plate portion 22 is positioned; and (ii) how the insert portion 24 can be sized and shaped so that the insert portion 24 can be positioned within the sinus tarsi and/or the subtalar joint 18 in a manner so as to correct and/or alter the alignment of the foot 10, i.e. with the top surface 236 (illustrated in FIG. 2A) being angled to allow the talus 14 to articulate over the top surface 236 in a corrected position to correct hyperpronation of the foot 10, and the bottom surface 238 (illustrated in FIG. 2A) being shaped to at least substantially match the anatomy of the calcaneus 16 in the area of the calcaneus 16 adjacent to which the insert portion 24 is positioned.

As with FIG. 1A, it should be appreciated that certain soft tissue structures and the fibula have been omitted from FIG. 1B for purposes of clarity, i.e. so that the subtalar plate implant 12 can be better seen implanted within the subtalar joint 18.

Figure 1C:
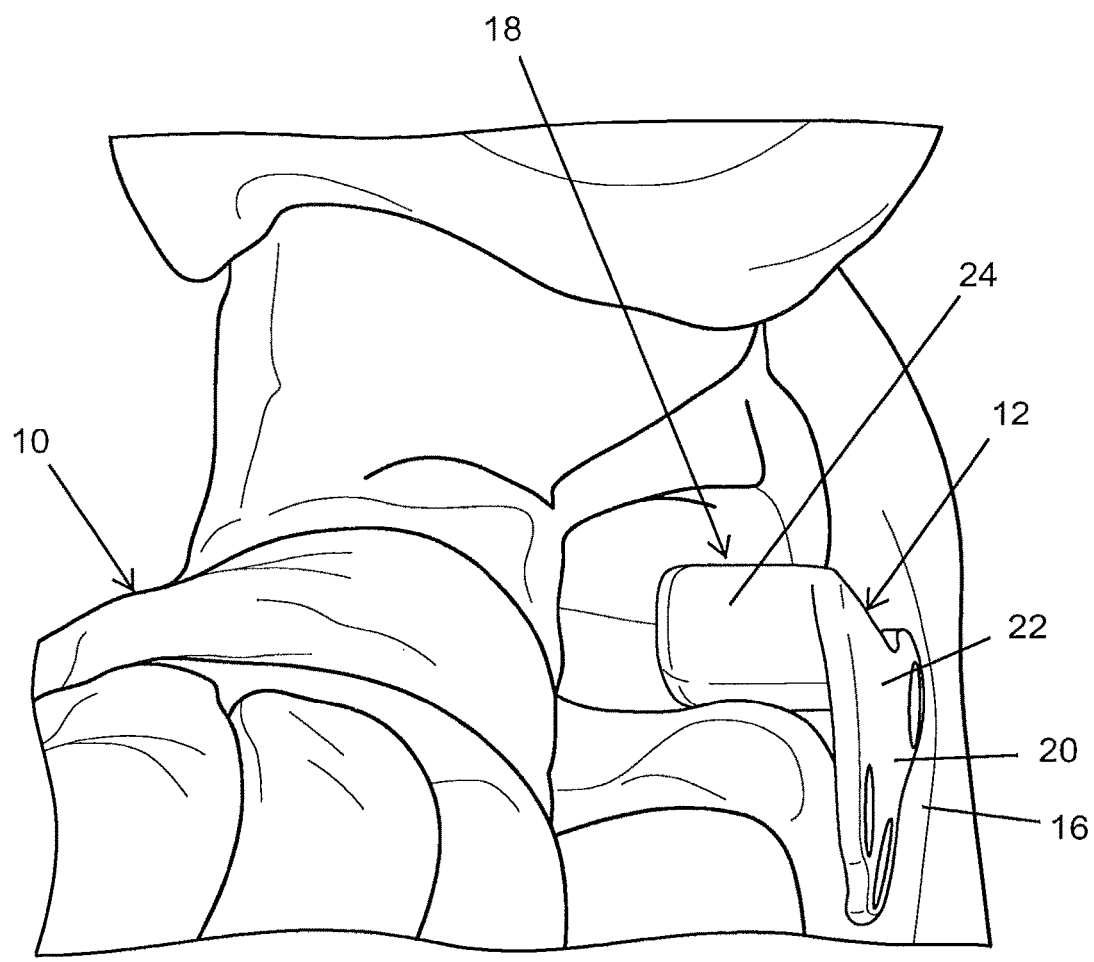
FIG. 1C is a front perspective view of a portion of the foot and the subtalar plate implant of FIG. 1A implanted therein.

FIG. 1C is a front perspective view of a portion of the foot 10 and the subtalar implant 12 of FIG. 1A implanted therein. Again, FIG. 1C illustrates still more clearly how the insert portion 24 of the implant body 20 is positioned securely within the sinus tarsi and/or within the subtalar joint 18 when the subtalar plate implant 12 is implanted within the foot 10. Additionally, FIG. 1C also more clearly illustrates the positioning of the plate portion 22 of the implant body 20 substantially adjacent to the lateral aspect of the calcaneus 16. Further, as noted above, the shape of the plate portion 22 may be designed to at least substantially match the anatomy, i.e. the shape, of the lateral aspect of the calcaneus 16 in the area where the subtalar plate implant 12 is implanted.

As with FIGS. 1A and 1B, it should be appreciated that certain soft tissue structures and the fibula have been omitted from FIG. 10 for purposes of clarity, i.e. so that the subtalar plate implant 12 can be better seen implanted within the subtalar joint 18.

Figure 2A:
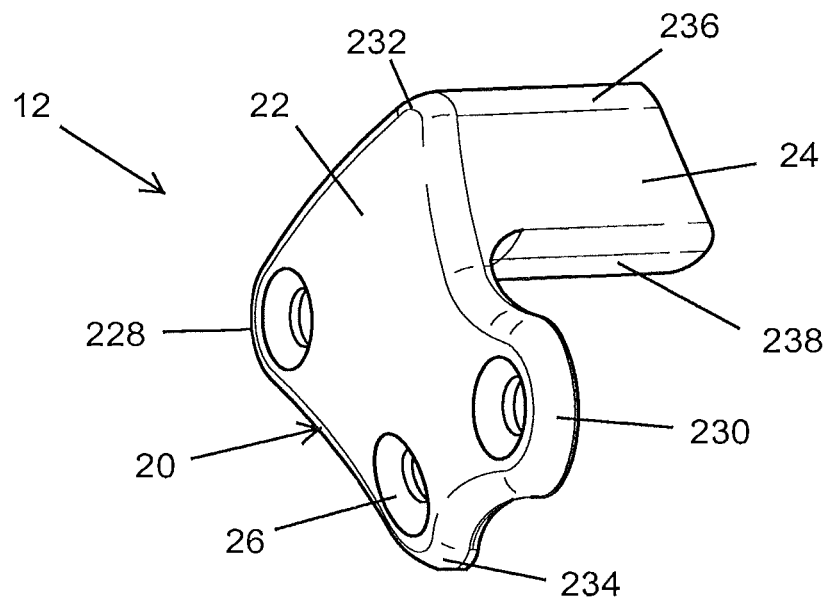
FIG. 2A is a simplified perspective view of the subtalar plate implant of FIG. 1A.
Figure 2B:
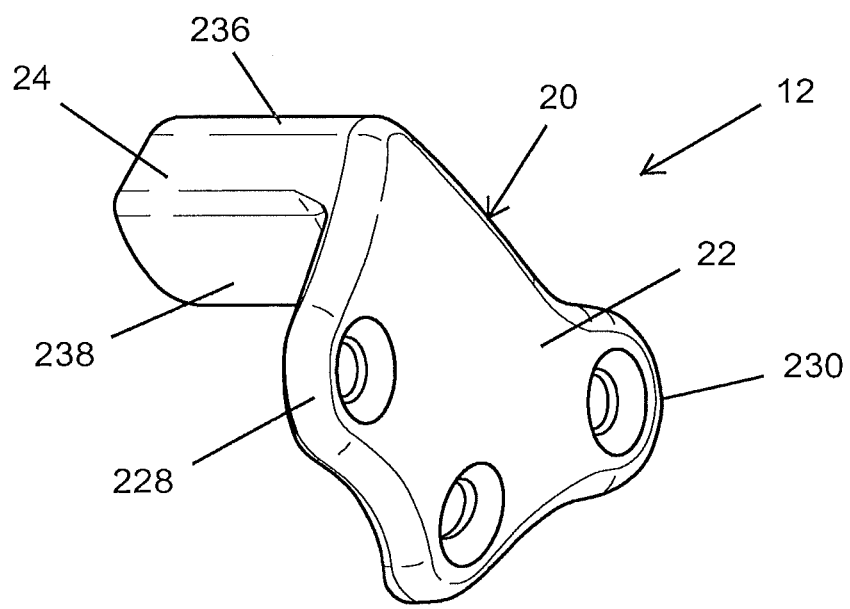
FIG. 2B is another simplified perspective view of the subtalar plate implant of FIG. 2A.
Figure 2C:
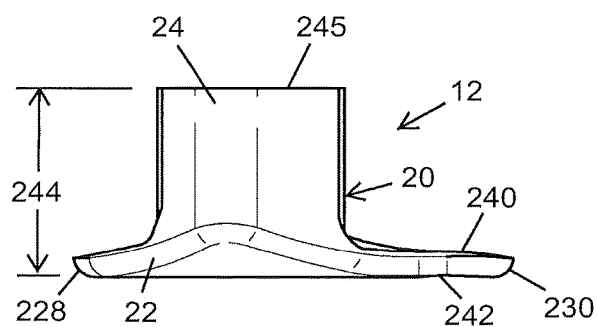
FIG. 2C is a simplified end view of the subtalar plate implant of FIG. 2A.
Figure 2D:
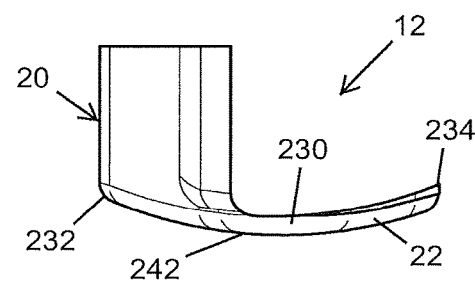
FIG. 2D is a simplified side view of the subtalar plate implant of FIG. 2A.
Figure 2E:
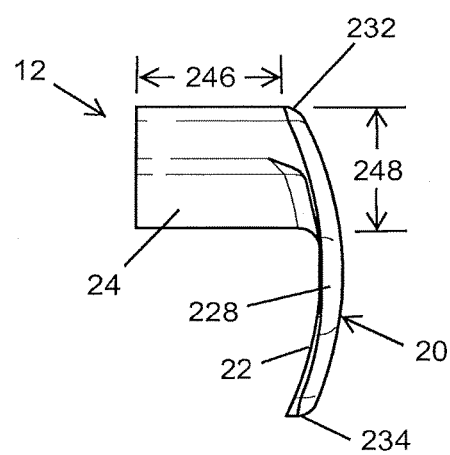
FIG. 2E is another simplified side view of the subtalar plate implant of FIG. 2A.
Figure 2F:
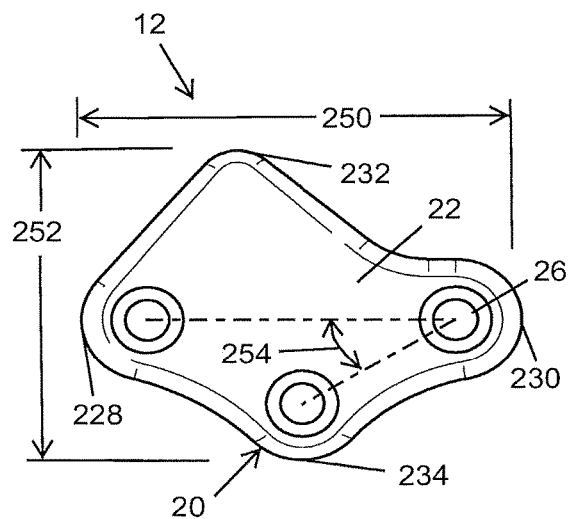
FIG. 2F is a simplified top view of the subtalar plate implant of FIG. 2A.

FIGS. 2A-2F are alternative views of the subtalar plate implant 12 of FIG. 1A that illustrate further details and features of the subtalar plate implant 12. In particular, FIG. 2A is a simplified perspective view of the subtalar plate implant 12 of FIG. 1A; FIG. 2B is another simplified perspective view of the subtalar plate implant 12 of FIG. 2A; FIG. 2C is a simplified end view of the subtalar plate implant 12 of FIG. 2A; FIG. 2D is a simplified side view of the subtalar plate implant 12 of FIG. 2A; FIG. 2E is another simplified side view of the subtalar plate implant 12 of FIG. 2A; and FIG. 2F is a simplified top view of the subtalar plate implant 12 of FIG. 2A.

It should be appreciated that the overall design and shape of the subtalar plate implant 12 can be varied from the specific design and shape illustrated herein without altering the intended breadth and scope of the present invention.

Initially, FIG. 2A illustrates certain details about the shape of the plate portion 22 of the implant body 20. For example, as illustrated in this embodiment, the plate portion 22 of the implant body 20 is somewhat amorphous-shaped, having a first end 228, an opposed second end 230, a top 232, and a bottom 234. Additionally, as illustrated, each of the first end 228, the second end 230, the top 232 and the bottom 234 can be somewhat curved or rounded for comfort of the patient into whom the subtalar plate implant 12 may be implanted. Further, in this embodiment, the three apertures 26 in the plate portion 22 are shown at and/or substantially adjacent to the first end 228, the second end 230 and the bottom 234, respectively, with each area of the apertures 26 jutting outward somewhat from the remainder of the plate portion 22.

Additionally, FIG. 2A (which looks more closely at the second end 230 of the plate portion 22 of the implant body 20) and FIG. 2B (which looks more closely at the first end 228 of the plate portion 22 of the implant body 20) illustrate certain details about the shape of the insert portion 24 of the implant body 20. For example, as illustrated in this embodiment, the insert portion 24 of the implant body 20 can extend approximately and/or substantially perpendicularly away from the plate portion 22. Further, the insert portion 24 is shown as having a top surface 236 and a bottom surface 238, with the top surface 236 extending in a generally downward direction further toward the second end 230 of the plate portion 22 (as shown in FIG. 2A) than toward the first end 228 of the plate portion 22 (as shown in FIG. 2B). In certain embodiments, as noted above, the top surface 236 of the insert portion 24 can be positioned substantially adjacent to a base of the talus 14 (illustrated, for example, in FIG. 1A), and may be angled to allow the talus 14 to articulate over the top surface 236 in a corrected position to correct hyperpronation of the foot 10 (illustrated, for example, in FIG. 1A). Moreover, in certain embodiments, the bottom surface 238 of the insert portion 24 may be shaped to at least substantially match the anatomy of the dorsal aspect of the calcaneus 16 (illustrated, for example, in FIG. 1A) in the area in which the bottom surface 238 of the insert portion 24 is positioned substantially adjacent to the calcaneus 16.

Referring now to FIG. 2C, this simplified end view of the subtalar plate implant 12 illustrates that the plate portion 22 includes an inner surface 240 that is adapted to face toward the calcaneus 16 (illustrated, for example, in FIG. 1A), and an outer surface 242 that is adapted to face away from the calcaneus 16, when the subtalar plate implant 12 is implanted in the foot 10 (illustrated, for example, in FIG. 1A) of a patient. Additionally, in one embodiment, as shown in FIG. 2C, the plate portion 22 can be curved slightly inwardly (i.e. concave curvature from the perspective of the outer surface 242) in the area of the plate portion 22 near the insert portion 24. The degree or extent of curvature of this section of the plate portion 22 can be varied as desired, such that the plate portion 22 from the first end 228 to the second end 230 can at least substantially match the shape, i.e. the bony contours, of the calcaneus 16 in the area adjacent to which the plate portion 22 is attached.

Further, FIG. 2C also illustrates that the implant body 20 can have a body height 244, which is the full height that the implant body 20 extends from the outer surface 242 of the plate portion 22 (i.e. near the first end 228 or the second end 230) to a distal end 245 of the insert portion 24 away from the plate portion 22. The body height 244 of the implant body 20 can be varied. In certain embodiments, the body height 244 can be between approximately 10.0 millimeters and 20.0 millimeters. Alternatively, the body height 244 can be greater than 20.0 millimeters or less than 10.0 millimeters.

As noted above, FIG. 2D is a simplified side view of the subtalar plate implant 12 of FIG. 2A. In particular, FIG. 2D illustrates the subtalar plate implant 12 from the perspective of looking in at the second end 230 of the plate portion 22 of the implant body 20. As shown in this embodiment, the plate portion 22 can be curved or arched (i.e. convex curvature from the perspective of the outer surface 242) from the top 232 to the bottom 234 of the plate portion 22. The degree or extent of curvature of this section of the plate portion 22 can be varied as desired, such that the plate portion 22 from the top 232 to the bottom 234 can at least substantially match the shape, i.e. the bony contours, of the calcaneus 16 (illustrated, for example, in FIG. 1A) in the area adjacent to which the plate portion 22 is attached on the calcaneus 16.

FIG. 2E provides another simplified side view of the subtalar plate implant 12 of FIG. 2A. In particular, FIG. 2E illustrates the subtalar plate implant 12 from the perspective of looking in at the first end 228 of the plate portion 22 of the implant body 20. As illustrated, FIG. 2E again illustrates the general curvature of the plate portion 22 from the top 232 to the bottom 234 of the plate portion 22.

Additionally, FIG. 2E further illustrates an insert length 246 (i.e. the distance the insert portion 24 extends away from the plate portion 22) and an insert width 248 (i.e. the distance the insert portion extends along and/or adjacent to the plate portion 22 away from the top 232 of the plate portion 22) of the insert portion 24 of the implant body 20. The insert length 246 and the insert width 248 can be varied. For example, in certain embodiments, the insert length 246 can be between approximately 9.0 millimeters and 13.0 millimeters, and the insert width 248 can be between approximately 7.5 millimeters and 11.5 millimeters. Alternatively, the insert length 246 can be greater than 13.0 millimeters or less than 9.0 millimeters, and/or the insert width 248 can be greater than 11.5 millimeters or less than 7.5 millimeters.

It should be appreciated that the insert length 246, as illustrated and described herein, essentially equates to a depth that the insert portion 24 is inserted into and/or within the sinus tarsi and/or the subtalar joint 18 (illustrated in FIG. 1A).

As noted above, FIG. 2F is a simplified top view of the subtalar plate implant 12 of FIG. 2A. In particular, FIG. 2F clearly illustrates the unique amorphous shape of this particular embodiment of the plate portion 22 of the implant body 20. Additionally, FIG. 2F illustrates an overall plate length 250 (i.e. from the first end 228 to the second end 230) and a plate width 252 (i.e. from the top 232 to the bottom 234) of the plate portion 22 of the implant body 20. For example, in certain embodiments, the plate length 250 can be between approximately 25.0 millimeters and 40.0 millimeters, and the plate width 252 can be between approximately 20.0 millimeters and 35.0 millimeters. Alternatively, the plate length 250 can be greater than 40.0 millimeters or less than 25.0 millimeters, and/or the plate width 252 can be greater than 35.0 millimeters or less than 20.0 millimeters.

Additionally, FIG. 2F further illustrates the orientation of the apertures 26 relative to one another. For example, in certain embodiments, when the apertures 26 near the first end 228 and the second end 230 of the plate portion 22 are viewed in a linear manner, the aperture 26 positioned near the bottom 234 of the plate portion 22 can have an angle of orientation 254 of between approximately fifteen and forty-five degrees relative to the line between the end-most apertures 26. More particularly, in one non-exclusive alternative embodiment, the aperture 26 positioned near the bottom 234 of the plate portion 22 can have an angle of orientation 254 of approximately thirty degrees relative to the line between the end-most apertures 26. Alternatively, the aperture 26 positioned near the bottom 234 of the plate portion 22 can have an angle of orientation 254 of greater than forty-five degrees or less than fifteen degrees relative to the line between the end-most apertures 26.

FIGS. 3A-3F are alternative views of another embodiment of the subtalar plate implant 312. In particular, FIG. 3A is a simplified perspective view of the subtalar plate implant 312; FIG. 3B is another simplified perspective view of the subtalar plate implant 312 of FIG. 3A; FIG. 3C is a simplified end view of the subtalar plate implant 312 of FIG. 3A; FIG. 3D is a simplified side view of the subtalar plate implant 312 of FIG. 3A; FIG. 3E is another simplified side view of the subtalar plate implant 312 of FIG. 3A; and FIG. 3F is a simplified top view of the subtalar plate implant 312 of FIG. 3A.

As illustrated, the subtalar plate implant 312 is somewhat similar to the subtalar plate implant 12 illustrated and described above in the previous embodiment. For example, the subtalar plate implant 312 comprises an implant body 320 including a plate portion 322 and an insert portion 324 that are somewhat similar to the implant body 20, the plate portion 22 and the insert portion 24 illustrated and described above. Additionally, the plate portion 322 again includes one or more apertures 326 that are sized and shaped to receive one or more attachers (not illustrated) that will be inserted into the calcaneus 16 (illustrated in FIG. 1A) to secure the subtalar plate implant 312 in place. In particular, as illustrated, the plate portion 322 can include three apertures 326, which can again be positioned substantially adjacent to the first end 328, the second end 330 and the bottom 334 of the plate portion 322. Further, the insert portion 324 of the implant body 320 is again to designed to be positioned securely within the sinus tarsi and/or within the subtalar joint 18 (illustrated in FIG. 1A) when the subtalar plate implant 312 is implanted within the foot 10 (illustrated in FIG. 1A).

Referring initially to FIG. 3A, this Figure illustrates certain details about the shape of the plate portion 322 of the implant body 320. In particular, the plate portion 322 again includes a first end 328, a second end 330, a top 332 and a bottom 334 that are generally designed in a similar manner to the previous embodiment. However, as illustrated, the plate portion 322 of the subtalar plate implant 312 in this embodiment has a slightly different overall shape than the plate portion 22 of the subtalar plate implant 12 in the previous embodiment. For example, as shown, the areas of the plate portion 322 that include the apertures 326 are somewhat less rounded and closer together relative to the other areas of the plate portion 322 as compared to the previous embodiment. Moreover, the apertures 326 are somewhat more aligned with one another across the plate portion 322. Stated in another manner, the aperture 326 positioned near the bottom 334 of the plate portion 322 can have an angle of orientation 354 (illustrated in FIG. 3F) relative to the line between the end-most apertures 326 that is somewhat less than in the previous embodiment. With this design, as more clearly illustrated in FIG. 3F, although the plate portion 322 is still somewhat amorphous-shaped, the plate portion 322 has a much more pronounced somewhat triangular shape. However, even with such changes in the design of the plate portion 322, the overall design and function of the subtalar plate implant 312 is substantially similar to the overall design and function of the previous embodiment, as illustrated and described above.

Additionally, FIG. 3A (which looks more closely at the second end 330 of the plate portion 322 of the implant body 320) and FIG. 3B (which looks more closely at the first end 328 of the plate portion 322 of the implant body 320) illustrate certain details about the shape of the insert portion 324 of the implant body 320. For example, as illustrated in this embodiment, the insert portion 324 again extends approximately and/or substantially perpendicularly away from the plate portion 322. Further, the insert portion 324 again includes a top surface 336 and a bottom surface 338, with the top surface 336 extending in a generally downward direction further toward the second end 330 of the plate portion 322 (as shown in FIG. 3A) than toward the first end 328 of the plate portion 322 (as shown in FIG. 3B). As with the previous embodiment, the top surface 336 of the insert portion 324 can be positioned substantially adjacent to a base of the talus 14 (illustrated in FIG. 1A), and may be angled to allow the talus 14 to articulate over the top surface 336 in a corrected position to correct hyperpronation of the foot 10 (illustrated in FIG. 1A). Moreover, the bottom surface 338 of the insert portion 324 may again be shaped to at least substantially match the anatomy of the dorsal aspect of the calcaneus 16 (illustrated in FIG. 1A) in the area in which the bottom surface 338 of the insert portion 324 is positioned substantially adjacent to the calcaneus 16.

As noted above, FIG. 3C is a simplified end view of the subtalar plate implant 312 of FIG. 3A. As illustrated in this embodiment, the plate portion 322 of the implant body 320 has a general shape or profile from the end view that is substantially similar to that of the previous embodiment. For example, the plate portion 322 can again be curved slightly inwardly (i.e. concave curvature from the perspective of the outer surface 342) in the area of the plate portion 322 near the insert portion 324. The degree or extent of curvature of this section of the plate portion 322 can be varied as desired, such that the plate portion 322 from the first end 328 to the second end 330 can at least substantially match the shape of the calcaneus 16 in the area adjacent to which the plate portion 322 is attached.

Additionally, FIG. 3C further illustrates that the insert portion 324 can include a concave groove 356 (illustrated in phantom) that is formed along the bottom surface 338 (illustrated in FIG. 3A) and substantially parallel to the plate portion 322 of the insert body 320. The design of the groove 356 can be varied as desired. For example, in certain embodiments, the groove 356 is sized and shaped to avoid and/or compensate for a bony ridge that can exist along the dorsal surface of the calcaneus 16 (illustrated in FIG. 1A). The groove 356 will be described in greater detail herein below.

As provided above, FIG. 3D is a simplified side view of the subtalar plate implant 312 of FIG. 3A; and FIG. 3E is another simplified side view of the subtalar plate implant 312 of FIG. 3A. In particular, FIGS. 3D and 3E illustrate more clearly various features regarding the design and positioning of the groove 356 that is formed along the bottom surface 338 of the insert body 324 of the insert body 320. For example, FIGS. 3D and 3E illustrate how the groove 356 is substantially parallel to the plate portion 322 of the insert body 320.

Additionally, In this embodiment, FIG. 3D illustrates that the groove 356 can have a groove depth 358 of between approximately 1.0 and 2.0 millimeters. Alternatively, the groove 356 can have a groove depth 358 that is greater than 2.0 millimeters or less than 1.0 millimeters.

Further, as shown, the groove 356 can be a rounded groove having a groove radius of curvature 360 of between approximately 2.0 and 3.0 millimeters. Alternatively, the groove 356 can have a different shape, e.g., a squared shape, and/or the groove 356 can have a groove radius of curvature 360 that is greater than 3.0 millimeters or less than 2.0 millimeters.

Still further, in certain embodiments, the groove 356 can be formed along the bottom surface 338 of the insert body 324 spaced apart from the plate portion 322. For example, as shown in the embodiment illustrated in FIG. 3D, a center of the groove 356 can be spaced apart from the plate portion 322 by a spacing distance 362 of between approximately 3.0 and 5.0 millimeters. Alternatively, the center of the groove 356 can be spaced apart from the plate portion 322 by a spacing distance 362 of greater than 5.0 millimeters or less than 3.0 millimeters.

As noted above, FIG. 3F is a simplified top view of the subtalar plate implant 312 of FIG. 3A. In particular, FIG. 3F illustrates the somewhat amorphous and somewhat triangular shape of the plate portion 322 of the implant body 320. Additionally, FIG. 3F illustrates an overall plate length 350 (i.e. from the first end 328 to the second end 330) and a plate width 352 (i.e. from the top 332 to the bottom 334) of the plate portion 322. For example, in this embodiment, the plate length 350 can be between approximately 20.0 millimeters and 35.0 millimeters, and the plate width 352 can be between approximately 15.0 millimeters and 25.0 millimeters. Alternatively, the plate length 350 can be greater than 35.0 millimeters or less than 20.0 millimeters, and/or the plate width 352 can be greater than 25.0 millimeters or less than 15.0 millimeters.

Further, FIG. 3F also illustrates that the bottom surface 338 of the insert portion 324 (illustrated in FIG. 3A) has a convex-shaped profile, which can be curved or rounded. For example, in certain embodiments, the bottom surface 338 of the insert portion 324 can have an insert radius of curvature 364 of between approximately 5.5 millimeters and 11.5 millimeters. Alternatively, the bottom surface 338 of the insert portion 324 can have an insert radius of curvature 364 of greater than 11.5 millimeters or less than 5.5 millimeters.

Additionally, FIG. 3F illustrates that the apertures 326 are substantially evenly spaced from one another when moving from the first end 328 to the second end 330. For example, in certain embodiments, the apertures 326 can be spaced apart from one another by an aperture spacing 366 of between approximately 5.5 millimeters and 13.0 millimeters. Alternatively, the apertures 326 can be spaced apart from one another by an aperture spacing 366 of greater than 13.0 millimeters or less than 5.5 millimeters.

Still further, as noted above, FIG. 3F further illustrates the orientation of the apertures 326 relative to one another. For example, in certain embodiments, the aperture 326 positioned near the bottom 334 of the plate portion 322 can have an angle of orientation 354 of between approximately ten and twenty degrees relative to a line drawn between the end-most apertures 326. More particularly, in one non-exclusive alternative embodiment, the aperture 326 positioned near the bottom 334 of the plate portion 322 can have an angle of orientation 354 of approximately fifteen degrees relative to the line between the end-most apertures 326. Alternatively, the aperture 326 positioned near the bottom 334 of the plate portion 322 can have an angle of orientation 354 of greater than twenty degrees or less than ten degrees relative to the line between the end-most apertures 326.

Figure 4A:
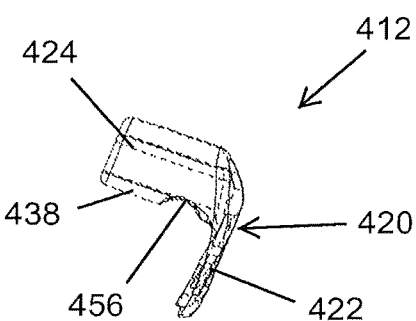
FIG. 4A is a simplified side view of still another embodiment of the subtalar plate implant.
Figure 4B:
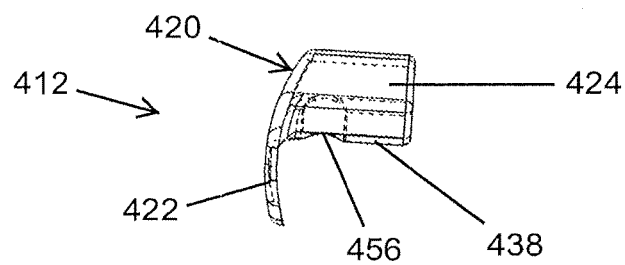
FIG. 4B is another simplified side view of the subtalar plate implant of FIG. 4A.
Figure 4C:
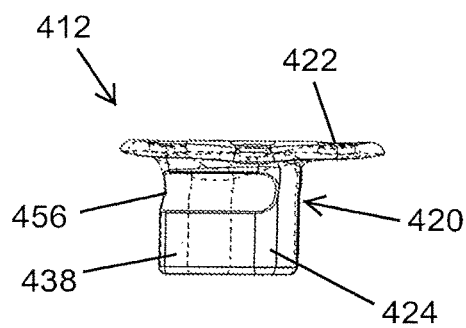
FIG. 4C is a simplified end view of the subtalar plate implant of FIG. 4A.
Figure 4D:
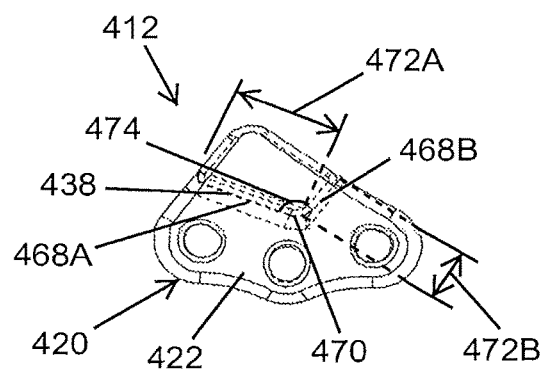
FIG. 4D is a simplified top view of the subtalar plate implant of FIG. 4A.

FIGS. 4A-4D are alternative views of still another embodiment of the subtalar plate implant 412. In particular, FIG. 4A is a simplified side view of the subtalar plate implant 412; FIG. 4B is another simplified side view of the subtalar plate implant 412 of FIG. 4A; FIG. 4C is a simplified end view of the subtalar plate implant of FIG. 4A; and FIG. 4D is a simplified top view of the subtalar plate implant 412 of FIG. 4A.

In this embodiment, the subtalar plate implant 412 is substantially similar to the subtalar plate implant 312 illustrated and described above in relation to FIGS. 3A-3F. More specifically, the subtalar plate implant 412 again comprises an implant body 420 including a plate portion 422 and an insert portion 424 that are substantially similar to the implant body 320, the plate portion 322 and the insert portion 324 illustrated and described above in relation to FIGS. 3A-3F. Additionally, the insert portion 424 again includes a groove 456 along the bottom surface 438 that is substantially parallel to and spaced apart from the plate portion 422, the groove 456 being sized and shaped to avoid and/or compensate for the bony ridge that can exist along the dorsal surface of the calcaneus 16 (illustrated in FIG. 1A).

However, in this embodiment, the insert portion 424 has a slightly different shape as compared to the previous embodiment. In particular, as illustrated most clearly in FIG. 4D, the bottom surface 433 of the insert portion 424 (illustrated, for example, in FIG. 4A) has a different shape than in the previous embodiment. For example, the bottom surface 438 no longer has a curved or rounded profile as in the previous embodiment. Rather, the bottom surface 438 of the insert portion 424 has a pair a flat segments, i.e. a first flat segment 468A and a second flat segment 468B that are angled relative to one another, and that are joined together by a rounded corner 470.

The design and relative orientation of the flat segments 468A, 468B can be varied to suit the specific requirements of the insert portion 424 of the implant body 420. For example, in certain embodiments, (i) the first flat segment 468A can have a first segment length 472A of between approximately 9.0 millimeters and 15.0 millimeters; (ii) the second flat segment 468B can have a second segment length 472B of between approximately 4.5 millimeters and 7.5 millimeters; and (iii) the flat segments 468A, 468B can be joined together by the rounded corner 470 having a corner angle 474 of between approximately ninety and one hundred twenty degrees. Alternatively, (i) the first flat segment 468A can have a first segment length 472A that is greater than 15.0 millimeters or less than 9.0 millimeters; (ii) the second flat segment 468B can have a second segment length 472B that is greater than 7.5 millimeters or less than 4.5 millimeters; and/or (iii) the flat segments 468A, 468B can be joined together by the rounded corner 470 having a corner angle 474 of greater than one hundred twenty degrees or less than ninety degrees.

Figure 5C:
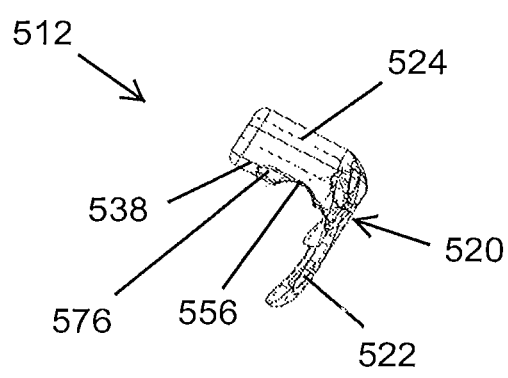
FIG. 5C is still another simplified side view of the subtalar plate implant of FIG. 5A and a plurality of attachers that are usable with the subtalar plate implant.
Figure 5C:
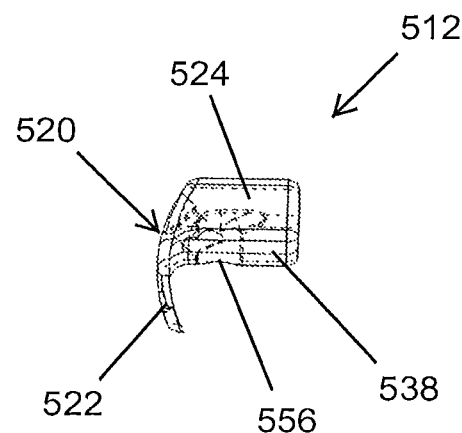
Figure 5C:
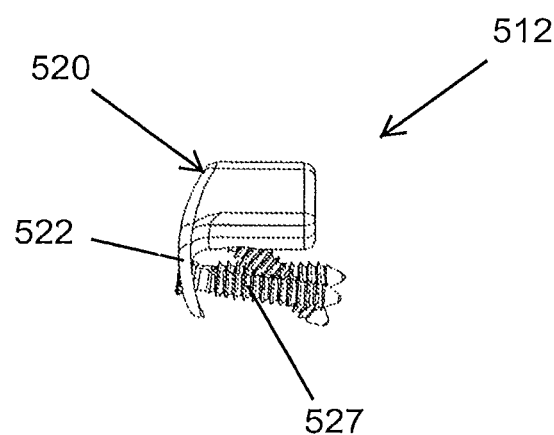
Figure 5D:
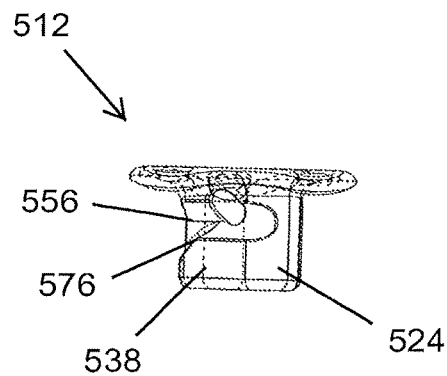
FIG. 5D is a simplified end view of the subtalar plate implant of FIG. 5A.
Figure 5E:
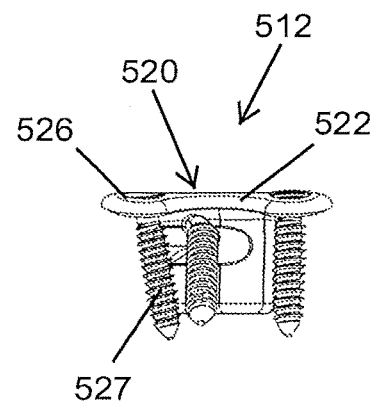
FIG. 5E is another simplified end view of the subtalar plate implant of FIG. 5A and the plurality of attachers of FIG. 5C.
Figure 5F:
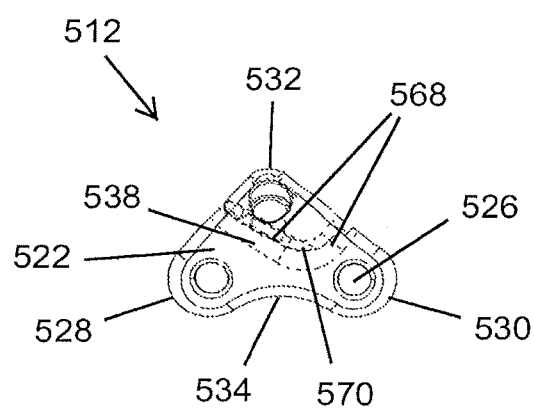
FIG. 5F is a simplified top view of the subtalar plate implant of FIG. 5A.
Figure 5G:
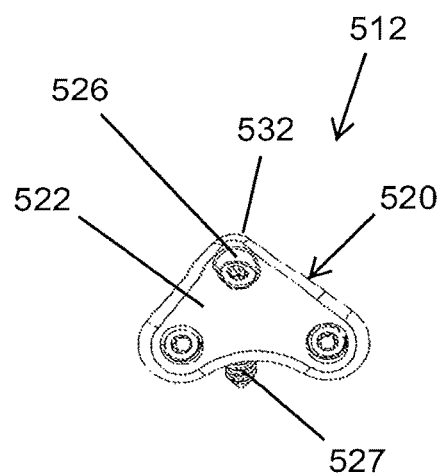
FIG. 5G is another simplified top view of the subtalar plate implant of FIG. 5A and the plurality of attachers of FIG. 5C.

FIGS. 5A-5G are alternative views of yet another embodiment of the subtalar plate implant 512. In particular, FIG. 5A is a simplified side view of the subtalar plate implant 512; FIG. 5B is another simplified side view of the subtalar plate implant 512 of FIG. 5A; FIG. 5C is still another simplified side view of the subtalar plate implant 512 of FIG. 5A and a plurality of attachers 527 that are usable with the subtalar plate implant 512; FIG. 5D is a simplified end view of the subtalar plate implant 512 of FIG. 5A; FIG. 5E is another simplified end view of the subtalar plate implant 512 of FIG. 5A and the plurality of attachers 527 of FIG. 5C; FIG. 5F is a simplified top view of the subtalar plate implant 512 of FIG. 5A; and FIG. 5G is another simplified top view of the subtalar plate implant 512 of FIG. 5A and the plurality of attachers 527 of FIG. 5C.

In this embodiment, the subtalar plate implant 512 is somewhat similar to the subtalar plate implants 312, 412 illustrated and described above in relation to FIGS. 3A-3F and 4A-4D, respectively. More specifically, initially referring to FIGS. 5A and 5B, the subtalar plate implant 512 again comprises an implant body 520 including a plate portion 522 and an insert portion 524 that are somewhat similar in design and function as compared to the corresponding features illustrated and described above in relation to FIGS. 3A-3F and FIGS. 4A-4D. Additionally, as shown, the insert portion 524 again includes a groove 556 along the bottom surface 538 that is substantially parallel to and spaced apart from the plate portion 522, the groove 556 being sized and shaped to avoid and/or compensate for the bony ridge that can exist along the dorsal surface of the calcaneus 16 (illustrated in FIG. 1A).

As noted above, FIG. 5B is a simplified side view of the subtalar plate implant 512. Additionally, FIG. 5C is a comparable side view of the subtalar plate implant 512, which shows the orientation of the attachers 527 as the attachers 527 extend through the apertures 526 (illustrated in FIG. 5F) for purposes of attaching the plate portion 522 of the implant body 520 to the lateral aspect of the calcaneus 16 (illustrated in FIG. 1A).

Further, as illustrated most clearly in FIG. 5F, similar to the embodiment illustrated in FIGS. 4A-4D, the bottom surface 538 of the insert portion 524 (illustrated more clearly in FIG. 5A) again has a pair a flat segments 568 that are angled relative to one another, and that are joined together by a rounded corner 570.

However, referring back to FIG. 5A, in this embodiment, the insert portion 524 further includes a cutout portion 576 along the bottom surface 538 that can be positioned substantially adjacent to the groove 556. The cutout portion 576 can be sized and shaped to avoid and/or compensate for a high spot that can exist along the dorsal surface of the calcaneus 16, such that the bottom surface 538 can more effectively and accurately match the shape of the dorsal surface of the calcaneus 16. Alternatively, the insert portion 524 can be designed without the cutout portion 576, and the high spot along the dorsal surface of the calcaneus 16 can be shaved down in preparation for implantation of the subtalar plate implant 512.

As provided above, FIG. 5D is a simplified end view of the subtalar plate implant 512. In particular, FIG. 5D further illustrates the design and positioning for the cutout portion 576 that can be formed along the bottom surface 538 of the insert portion 524 substantially adjacent to the groove 556. Additionally, FIG. 5E is a comparable end view of the subtalar plate implant 512, which shows the orientation of the attachers 527 as the attachers 527 extend through the apertures 526 for purposes of attaching the plate portion 522 of the implant body 520 to the lateral aspect of the calcaneus 16 (illustrated in FIG. 1A).

Additionally, as shown most clearly in FIG. 5F, the plate portion 522 can have a slightly different shape than the previous embodiments, and the plate portion 522 can include one or more apertures 526 that are positioned in a different manner than in the previous embodiments. More specifically, the plate portion 522 again includes a first end 528, a second end 530, a top 532 and a bottom 534; but in this embodiment, the bottom 534 of the plate portion 522 extends and/or curves in an inward manner relative to the remainder of the plate portion 522, as opposed to jutting out slightly as it did in the previous embodiments. With this design, although the plate portion 522 is still somewhat amorphous-shaped, the plate portion 522 can also be seen as having a shape somewhat similar to that of the head of an arrow.

Further, as noted, the positioning of the apertures 526 can be different than in the previous embodiments. In this embodiment, the plate portion 522 again includes apertures 526 located substantially adjacent to the first end 528 and the second end 530 of the plate portion 522, but the plate portion 522 further includes an aperture 526 positioned substantially adjacent to the top 532 of the plate portion 522 (i.e. as opposed to substantially adjacent to the bottom of the plate portion as can be seen in the previous embodiments). Each of the apertures 526 is again adapted to receive an attacher 527 (illustrated, for example, in FIG. 5G) so as to effectively secure the plate portion 522 of the subtalar plate implant 512 adjacent to the lateral aspect of the calcaneus 16 (illustrated in FIG. 1A) in the area where the subtalar plate implant 512 is implanted.

FIG. 5G is a comparable top view of the subtalar plate implant 512, which shows the orientation of the attachers 527 as the attachers 527 extend through the apertures 526 for purposes of attaching the plate portion 522 of the implant body 520 to the lateral aspect of the calcaneus 16 (illustrated in FIG. 1A). With this design, by securing the plate portion 522 to the calcaneus 16 with an attacher 527 substantially adjacent to the top 532 of the plate portion 522, the insert portion 524 (illustrated in FIG. 5A) may be held more securely within the subtalar joint 18 (illustrated in FIG. 1A), i.e. there is less ability of the insert portion 524 to potentially move slightly in and out of the subtalar joint 18 during motion of the foot 10 (illustrated in FIG. 1A).

As illustrated, and as described in detail herein, the overall design and shape of the subtalar plate implant 12 is designed (e.g., with rounded edges and corners, with smooth surfaces, etc.) to suit the comfort of the patient into whom the subtalar plate implant 12 will be implanted, as well as to perform the desired function of correcting the hyperpronation of the foot 10 (illustrated, for example, in FIG. 1A) of the patient. For example, as described in detail herein, in some embodiments, the shape of the plate portion 22 of the implant body 20 can be designed to at least substantially match the lateral aspect of the calcaneus 16 (illustrated, for example, in FIG. 1A) in the area adjacent to which the plate portion 22 is secured to the calcaneus 16. Moreover, as noted above, the top surface 236 of the insert portion 24 may be angled to allow the talus 14 (illustrated, for example, in FIG. 1A) to articulate over the top surface 236 in a corrected position to correct hyperpronation of the foot 10; and the bottom surface 238 of the insert portion 24 may be shaped to at least substantially match the anatomy of the dorsal aspect of the calcaneus 16 in the area in which the bottom surface 238 of the insert portion 24 is positioned substantially adjacent to the calcaneus 16.

Additionally, it should be appreciated that the various features and aspects of the subtalar plate implant 12, 312, 412, 512 that have been illustrated and described herein in various embodiments can be combined in any suitable manner to form new embodiments without altering the intended scope and breadth of the present invention.

While a number of exemplary aspects and embodiments of a subtalar plate implant 12, 312, 412, 512 have been shown and disclosed herein above, those of skill in the art will recognize certain modifications, permutations, additions and sub combinations thereof. It is therefore intended that the subtalar plate implant 12, 312, 412, 512 shall be interpreted to include all such modifications, permutations, additions and sub-combinations as are within their true spirit and scope, and no limitations are intended to the details of construction or design herein shown.

What is claimed is:

1. A subtalar plate implant for implanting in a foot, the foot including a talus, a calcaneus, and a subtalar joint at the meeting point of the talus and the calcaneus, the subtalar plate implant comprising:
   a plate portion including a first and second end, a top and a bottom, that is selectively positionable substantially adjacent to a lateral aspect of the calcaneus, the plate portion including an aperture positioned substantially adjacent to each of the first and second end that is adapted to receive an attacher for selectively attaching the plate portion to the lateral aspect of the calcaneus; and
   an insert portion that is connected to the plate portion, the insert portion being at least partially positionable within the subtalar joint when the subtalar plate implant is implanted in the foot; and
   wherein a shape of the plate portion and the insert portion can be varied to match anatomical features of the talus and the calcaneus in specific areas where the subtalar plate implant is being implanted.

2. The subtalar plate implant of claim 1 wherein the plate portion is shaped to substantially match a shape of the lateral aspect of the calcaneus adjacent to which the plate portion is selectively positionable.

3. The subtalar plate implant of claim 1 wherein the insert portion includes a top surface that is selectively positionable substantially adjacent to a base of the talus, the top surface being angled to allow the talus to articulate over the top surface.

4. The subtalar plate implant of claim 1 wherein the insert portion includes a bottom surface that is selectively positionable substantially adjacent to a dorsal surface of the calcaneus.

5. The subtalar plate implant of claim 4 wherein the insert portion includes a groove that is formed along the bottom surface.

6. The subtalar plate implant of claim 5 wherein the groove is formed along the bottom surface substantially parallel to the plate portion.

7. The subtalar plate implant of claim 4 wherein the bottom surface is substantially convex-shaped.

8. The subtalar plate implant of claim 4 wherein the bottom surface includes a pair of flat segments that are angled relative to one another.

9. The subtalar plate implant of claim 1 wherein the plate portion and the insert portion are formed from one or more of a metallic material and a polymeric material.

10. A subtalar plate implant for correcting hyperpronation of a foot, the foot including a talus, a calcaneus, and a subtalar joint at a meeting point of the talus and the calcaneus, the subtalar plate implant comprising:
    an insert portion that is at least partially positionable within the subtalar joint when the subtalar plate implant is implanted in the foot, the insert portion including a bottom surface that is selectively positionable substantially adjacent to a dorsal surface of the calcaneus, and the insert portion including a groove that is formed along the bottom surface;
    an implant body featuring a substantially smooth surface and one or more round edges so as to inhibit any discomfort felt by a patient; and
    wherein a shape of the plate portion and the insert portion can be varied to match anatomical features of the talus and the calcaneus in specific areas where the subtalar plate implant is being implanted.

11. The subtalar plate implant of claim 10 wherein the bottom surface is substantially convex-shaped.

12. The subtalar plate implant of claim 10 wherein the bottom surface includes a pair of flat segments that are angled relative to one another.

13. The subtalar plate implant of claim 10 wherein the insert portion includes a top surface that is selectively positionable substantially adjacent to a base of the talus, the top surface being angled to allow the talus to articulate over the top surface.

14. The subtalar plate implant of claim 10 further comprising a plate portion that is connected to the insert portion, the insert portion extending substantially perpendicularly away from the plate portion, wherein the plate portion is selectively positionable substantially adjacent to a lateral aspect of the calcaneus.

15. The subtalar plate implant of claim 14 wherein the plate portion includes an aperture that is adapted to receive an attacher for selectively attaching the plate portion to the lateral aspect of the calcaneus.

16. The subtalar plate implant of claim 14 wherein the groove is formed along the bottom surface substantially adjacent to the plate portion.

17. A subtalar plate implant for correcting hyperpronation of a foot, the foot including a talus, a calcaneus, and a subtalar joint at a meeting point of the talus and the calcaneus, the subtalar plate implant comprising:
    a plate portion that is selectively positionable substantially adjacent to a lateral aspect of the calcaneus, the plate portion being substantially amorphous-shaped, the plate portion including a first end, a second end, a top and a bottom, each of which are curved in shape for patient comfort, wherein the plate portion includes an aperture that is positioned substantially adjacent to each of the first end and the second end, and wherein the plate portion includes an aperture that is positioned substantially adjacent to one of the top and the bottom, each of the apertures being adapted to receive an attacher for selectively attaching the plate portion to the lateral aspect of the calcaneus; and an insert portion that is connected to the plate portion, the insert portion extending substantially perpendicularly away from the plate portion, the insert portion including a top surface and a bottom surface, wherein the top surface is selectively positionable substantially adjacent to a base of the talus, the top surface being angled to allow the talus to articulate over the top surface; and wherein the bottom surface is selectively positionable substantially adjacent to a dorsal surface of the calcaneus, the insert portion including a groove that is forming along the bottom surface substantially parallel to the plate portion; and wherein a shape of the plate portion and the insert portion can be varied to match anatomical features of the talus and the calcaneus in specific areas where the subtalar plate implant is being implanted.

\* \* \* \* \*